US009185922B2

(12) United States Patent
Eino et al.

(10) Patent No.: US 9,185,922 B2
(45) Date of Patent: Nov. 17, 2015

(54) DAIRY PRODUCT

(75) Inventors: Moni Eino, Mississauga (CA); Larry Milligan, Guelph (CA); John Osborne, Elmira (CA)

(73) Assignee: UNIVERSITY OF GUELPH, Guelph, Ontario (CA)

( * ) Notice: Subject to any disclaimer, the term of this patent is extended or adjusted under 35 U.S.C. 154(b) by 248 days.

(21) Appl. No.: 13/046,361

(22) Filed: Mar. 11, 2011

(65) Prior Publication Data

US 2011/0287132 A1 Nov. 24, 2011

Related U.S. Application Data

(63) Continuation-in-part of application No. 11/445,186, filed on Jun. 2, 2006, now abandoned.

(51) Int. Cl.
| | |
|---|---|
| A23C 9/13 | (2006.01) |
| A23C 9/152 | (2006.01) |
| A23C 13/12 | (2006.01) |
| A23C 15/12 | (2006.01) |
| A23C 19/05 | (2006.01) |
| A23C 19/076 | (2006.01) |
| A23G 9/36 | (2006.01) |
| A23K 1/16 | (2006.01) |
| A23K 1/18 | (2006.01) |
| A23L 1/30 | (2006.01) |
| A61K 35/20 | (2006.01) |
| A23G 9/40 | (2006.01) |

(52) U.S. Cl.
CPC ............. *A23C 9/1315* (2013.01); *A23C 9/1528* (2013.01); *A23C 13/12* (2013.01); *A23C 15/126* (2013.01); *A23C 19/054* (2013.01); *A23C 19/076* (2013.01); *A23G 9/36* (2013.01); *A23G 9/40* (2013.01); *A23K 1/164* (2013.01); *A23K 1/1813* (2013.01); *A23L 1/3008* (2013.01); *A61K 35/20* (2013.01); *A23C 2230/10* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,533,557 A | 8/1985 | Maruyama et al. | |
| 5,616,339 A * | 4/1997 | Prud'Homme et al. | 424/438 |
| 5,932,257 A | 8/1999 | Wright et al. | |
| 5,976,606 A | 11/1999 | Koga et al. | |
| 5,985,348 A | 11/1999 | Barclay | |
| 6,200,624 B1 | 3/2001 | Mazer et al. | |
| 6,428,832 B2 | 8/2002 | Van Den Burg et al. | |
| 6,596,302 B2 | 7/2003 | O'Connor et al. | |
| 6,602,537 B1 | 8/2003 | Cummings et al. | |
| 6,727,373 B2 | 4/2004 | Bijl et al. | |
| 7,001,610 B2 | 2/2006 | Stewart | |
| 7,063,855 B2 | 6/2006 | Hjaltason et al. | |
| 2003/0007998 A1 * | 1/2003 | Block et al. | 424/442 |
| 2003/0198730 A1 | 10/2003 | Stewart | |
| 2003/0211221 A1 | 11/2003 | Abril et al. | |
| 2004/0058003 A1 | 3/2004 | Rosenberg et al. | |
| 2004/0131727 A1 | 7/2004 | Nakajima et al. | |
| 2004/0202769 A1 | 10/2004 | Stewart | |
| 2004/0265462 A1 | 12/2004 | Carlson | |
| 2005/0031672 A1 * | 2/2005 | Duarte Lanna et al. | 424/442 |

FOREIGN PATENT DOCUMENTS

| | | |
|---|---|---|
| CA | 2208392 | 9/2002 |
| CA | 2444189 | 10/2002 |
| CA | 2524451 | 11/2004 |
| JP | 63294747 A * | 12/1988 |
| WO | WO 00/44239 | 8/2000 |
| WO | WO 02/00028 | 1/2002 |

OTHER PUBLICATIONS

Staples et al. Improving Cow Fertility through Fish Meal Supplementation, University of Florida, Feb. 2002; p. 95-99.*
Gonzales et al., Monensin toxicosis in a dairy herd; Can Vet J 2005;46:910-912.*
Chhabra, Antimicrobial and Antioxidant Properties of Chitosan, Thesis Submitted to the Graduate Faculty of the University of Georgia, Athens, Georgia, 2004.*
Shahidi, F. "Seafood processing by-products." Seafoods: Chemistry, Processing Technology and Quality. Springer US, 1994. 320-334.*
Allan et al. The fungicidal Effect of Chitosan on Fungi of Varying Cell Wall Composition; Expermintal Mycology 3, 285-287 (1979).*
Staples et al. Improving Cow Fertility through Fish Meel Supplementation University of Guelph, Feb. 22, 2002:p. 95-99.
US Non-Final Office Action dated Sep. 14, 2010 Issued in the Parent Case—U.S. Appl. No. 11/445,186, filed Jun. 2, 2006.
JP 8 336360 A (Kanagawa Kagau Kenkyusho KK; Sano Shokukin Kagaku Kendyusho) Dec. 24, 1996 *abstract*.
Boris J et al: "A randomized Controlled Trial of the Effect of Fish Oil Supplementation in Late Pregnancy and Early Lactation on the N-3 Fatty Acid Content in Human Breast Milk", Lipids, Springer, US vol. 39, No. 12, Dec. 1, 2004, pp. 1191-1196.
Wright T C et al: "Effect of Combinations of Fish Meal and Feather Meal on Milk Fatty Acid Content and Nitrogen Utilization in Dairy Cows", Journal of Dairy Science, vol. 86, No. 3, 2003, pp. 861-869.
Franklin S T et al: "Dietary Marine Algae (Schizochytrium SP.) Increases Concentrations of Conjugated Linoleic, Docosahexaenoic and Transvaccenic Acids in Milk of Dairy Cows", The Journal of Nutrition, Wistar Institute of Anatomy and Biology, vol. 129, No. 11, Nov. 1, 1999, pp. 2048-2054.
Kammerlehner J: "Vorkommen Von Omega-3-Fettsaeuren Im Milchfett—IHRE Gesundheitliche Bedeutung", Deutsche Milchwirtschaft, Hildesheim, DE, vol. 46, No. 2, Jan. 1, 1995, pp. 68-70, No Translation.

* cited by examiner

*Primary Examiner* — Michael G Hartley
*Assistant Examiner* — Nabila Ebrahim (57) ABSTRACT

The present invention provides a novel dairy product comprising naturally secreted mammalian milk which comprises at least about 0.3% long chain omega-3 fatty acids/g of total milk fatty acids. A method of obtaining the milk is also provided which includes feeding a supplement to a mammal comprising a source of long chain omega-3 fatty acids that comprises at least about 2-10% long chain omega-3 fatty acids wt/wt and a protectant that protects against fatty acid biodehydrogenation.

4 Claims, 4 Drawing Sheets

Note: Group 1 - lignin from grass, Group 2 - lignin from wood, Group 3 - chitosan

Figure 3

Sample #865

| Lipid Fraction | %DHA (%) | Fat % | DHA g/100g |
|---|---|---|---|
| FFA | 48.99 | 0.25 | 0.12 |
| TG | 2.98 | 4.14 | 0.12 |
| PL | 29.99 | 2.64 | 0.79 |
| Avg/Total | 14.76 | 7.03 | 1.04 |
| complete | 12.97 | 7.61 | 0.99 |

Sample #867

| Lipid Fraction | %DHA (%) | Fat % | DHA g/100g |
|---|---|---|---|
| FFA | 31.62 | 0.78 | 0.25 |
| TG | 5.66 | 4.34 | 0.25 |
| PL | 32.83 | 2.25 | 0.74 |
| Avg/Total | 16.70 | 7.37 | 1.23 |
| complete | 14.02 | 7.07 | 0.99 |

Sample #866

| Lipid Fraction | %DHA (%) | Fat % | DHA g/100g |
|---|---|---|---|
| FFA | 45.06 | 0.45 | 0.20 |
| TG | 3.71 | 5.45 | 0.20 |
| PL | 34.22 | 2.89 | 0.99 |
| Avg/Total | 15.86 | 8.79 | 1.39 |
| complete | 13.64 | 8.8 | 1.2 |

DAIRY PRODUCT

FIELD OF INVENTION

The present invention relates to dairy products and food products derived from those dairy products that contain elevated levels of long-chain omega-3 fatty acids (LCn-3FA), and in particular, docosahexaneoic acid (DHA; C-22:6 n-3), eicosapentanoic acid (EPA; 20:5 n-3) and docosapentanoic acid (DPA; 22:5 n-3). The invention also relates to a composition and method for feeding dairy cattle to achieve enhanced levels of long-chain omega-3 fatty acids in milk.

BACKGROUND OF THE INVENTION

Long-chain omega-3 fatty acids (LCn-3FA) are important nutrients necessary for maintaining human health from conception to childhood and throughout life. DHA, an important LCn-3FA, is a major component of nerve, brain and eye tissue. DHA has been associated with a variety of human health benefits including the prevention and management of cardiovascular disease in adults, improved visual acuity in infants, management of inflammatory disease in adults and help with attention deficit disorder. Other LCn-3FA that have been shown to have beneficial physiological effects when consumed, include EPA and DPA.

The diets of people in many countries and cultures have been shown to be deficient in LCn-3FA. The American Heart Association recommends the daily consumption of fish or fish oil supplement for adults to achieve a combined DHA and EPA intake of about 900 mg/day. The current mean intake of DHA and EPA (combined) for adults in North America (which includes about one fish serving every 10 days) is approximately 130 mg/day or 14% of the target intake.

LCn-3FAs have been shown to be required nutrients for optimal maturation of visual and cortical function in human infants. Evidence suggests that breast-fed infants exhibit enhanced cognitive development over formula-fed infants, and it has been suggested that the deficiency of LCn-3FA such as DHA in infant formulas and cow's milk may be linked to cognitive development.

To address these issues, it would be desirable to add LCn-3FA and/or sources of LCn-3FA to ingestable formulations. However, several characteristics make the inclusion LCn-3FA in good tasting food a challenge. LCn-3FA such as DHA, EPA, and DPA are typically derived from fatty fish and are often used in the form of fish oil with the attendant flavour and odour being major barriers to use. Additionally, these fatty acids contain multiple conjugated double bonds and, thus, are extremely susceptible to oxidation and rancidity rendering their purification, concentration and storage very difficult As a result, LCn-3FA-containing oil from fish, or in vitro cultured algae, which is subjected to concentration, purification, and anti-oxidation is very costly to produce, further limiting its use.

Various LCn-3FA-containing nutritional supplements have been developed. These are usually provided in a compressed tablet or capsule format. While these supplements do provide health benefits, they are still associated with a fishy flavor. An increasing area of interest is food products such as spreads like margarine, instant powder concentrates, liquid egg preparations and bread-containing LCn-3FA. It has been found, however, that while food products with strong flavors and/or sweetness can significantly mask the unpleasant fishy taste, milder tasting products are unsuitable for this type of enrichment due to poor palatability. In addition, encapsulated oil tends to separate, particularly from liquid products.

Bovine milk and dairy products play an important role in human health and nutrition. The Canada Food Guide recommends the daily consumption of dairy products for people of all ages. Consumption of milk is particularly important for children. In fact, milk is the primary source of fatty acids for children. Thus, it would be desirable to provide LCn-3FA-enhanced dairy products for consumption. However, addition of exogenous fish oil to milk results in a foul taste.

Several attempts have been made to provide milk-like products or other products that contain LCn-3FA.

U.S. Pat. No. 5,976,606 provides a process for producing a DHA-containing tofu or soybean milk drink, or a dry powder thereof that is stable and inexpensive. A DHA-containing fish oil emulsion is prepared by mixing soybean milk with DHA-containing fish oil at a weight ratio of 1:0.2 to 1:1, and stirring the mixture. The soybean milk drink can be produced by further diluting this emulsion with soybean milk to give a predetermined DHA concentration. DHA-containing tofu can be produced by coagulating the soybean milk containing this emulsion with the addition of a coagulant. Since the same soybean milk as the starting material of tofu or soybean milk drink is used as an emulsifying agent, even if DHA is contained at a high concentration, this does not influence the taste or properties of the product. A dry powder can be obtained by freeze-drying, vacuum drying or spray-drying this tofu or soybean milk drink as required.

U.S. Pat. No. 6,428,832 relates to a process for the preparation of a PUFA-containing food, such as an infant formula, in which a composition comprising a PUFA is added at a late stage of the infant formula preparation process. In this way, the PUFA's are minimally exposed to conditions during the process that induce degradation of the PUFA's.

U.S. Pat. No. 6,596,302 provides methods for providing nutrition and for enhancing neurological development of preterm infants. Also disclosed is an improved nutritional composition containing specified amounts of DHA and arachadonic acid (AA), as well as the respective precursors thereof, fatty acids, alpha-linolenic acid (ALA) and linoleic acid (LA). The method involves feeding these nutrient-enriched formulae for an extended feeding regimen, typically until at least 3 months corrected age (CA), preferably to 6 or even 12 months CA.

U.S. Pat. No. 6,727,373 discloses a microbial polyunsaturated fatty acid (PUFA)-containing oil with a high triglyceride content and a high oxidative stability. In addition, a method is described for the recovery of such oil from a microbial biomass derived from a pasteurized fermentation broth, wherein the microbial biomass is subjected to extrusion to form granular particles, dried and the oil then extracted from the dried granules using an appropriate solvent.

United States Patent Application No. 2004/0131727 provides dairy products containing fish-oil originated EPA and/or DHA which exhibits oxidation and emulsification stability. The milk is acidified by addition of an acid, fermented milk, or acidified milk containing any of the milk acidified by addition of an acid and the fermented milk. The acidified milk contains EPA and/or DHA as fish oil, preferably purified fish oil or fish oil containing EPA and/or DHA in an adjusted amount. The acidified milk is produced through an emulsification process. Preferably, the emulsification is performed after a fermentation process of the acidified milk process through a two-stage emulsification process.

United States Patent Application No. 2003/0211221 describes a composition comprising a polyunsaturated fatty acid (PUFA) and a protective fat, wherein the PUFA comprises an omega-3 PUFA, omega-6 PUFA or a combination thereof. The protective fat may be a triacylglycerol containing at least two and preferably three saturated fatty acids, or a functional derivative thereof.

United States Patent Application No. 2004/0265462 provides an infant milk formula having long chain polyunsaturated fatty acids, sialic acids, and cholesterol.

U.S. Pat. No. 6,200,624 describes the use of triglycerides containing fatty ester moieties that include arachidonic acid (AA) and docosahexaenoic acid (DHA) in enteral nutritionals or nutritional supplements. These triglycerides are derived from lipid mixtures which have high levels of sterols and phosphorous. A preferred embodiment of the invention comprises an infant or enteral nutritional that comprises a lipid source derived from egg yolk. The lipid source derived from egg yolk is prepared by transesterification or hydrolysis, subjecting the mixture to distillation, and esterification with glycerin to result in a triglyceride containing the desired fatty acids of AA and DHA and little or no sterols and phosphorus.

Milk fat is synthesized either from FA which are taken up from the blood (60%) or by de novo synthesis in the mammary gland (40%). LC n-3 FAs are not synthesized by ruminant tissues, so the concentration of LCn-3FA in milk is dependent on how much is ingested (from the diet) and on the amount that flows out of the rumen unaltered. The rumen, however, is a site of intense microbial lipid metabolism. Under normal conditions, unsaturated FAs like LC n-3 FAs are hydrogenated by the rumen microbial population via a process called biohydrogenation. This results in a very low level of LC n-3 FAs reaching the small intestine where they can be absorbed.

During the various steps of lipid biohydrogenation (hydrolysis, isomerization and hydrogenation) in the rumen, numerous intermediate compounds are produced. Research has shown that some FA isomers (e.g. trans-10, cis-12 CLA) can cause significant milk fat depressions (up to 25% reduction) even when small amounts reach the small intestine. The presence of certain FA in the mammary gland is thought to interfere with enzymes (Acetyl CoA carboxylase, fatty acid synthase, stearolyl CoA desaturase) involved in de novo fatty acid synthesis. Thus, the problem of getting milk enriched for LC n-3 FAs without causing a significant decrease in total milk fat levels is not easily solved.

U.S. Pat. No. 5,932,257 describes a feed additive, for milk-producing livestock such as cows, comprising a source of DHA and an inhibitor of microbial degradation of DHA in the rumen comprising feathermeal. While administration of this feed additive to cattle results in a milk product that contains DHA, greater levels of DHA in milk are desirable Accordingly, despite the foregoing, there remains a need to develop a food product comprising elevated levels of one or more long-chain omega-3 fatty acids.

SUMMARY OF THE INVENTION

A novel dairy product comprising naturally secreted mammalian milk has now been developed that contains elevated levels of at least one long-chain omega-3 fatty acid (LCn-3FA), for example, at least one of DHA, EPA, and/or DPA. Also provided is a feed additive to be fed to a ruminant mammal to achieve such a dairy product from milk naturally secreted from the mammal. Methods of promoting health and preventing or treating diseases by ingestion of the LCn-3FA-enriched dairy product are also provided.

In one aspect, the invention provides a dairy product comprising naturally secreted mammalian milk. The milk comprises at least about 0.3% long chain omega-3 fatty acids/g of total milk fatty acids. In a preferred embodiment, the milk comprises at least about 0.3% DHA/g of total milk fatty acids (FA), preferably about 0.35% DHA/g of total milk fatty acids (FA) and more preferably about 0.4% DHA/g of total milk fatty acids (FA).

In another aspect, a dairy product comprising at least about 0.1% EPA/g of total milk FA is provided.

In a further aspect, a dairy product comprising elevated (at least about 0.1%) DPA as a percent of weight of total milk FA is provided.

In a preferred aspect, a dairy product comprising at least about 0.3% DHA and at least about 0.1% EPA/g total milk FA is provided.

In a preferred embodiment, the dairy product comprises a product selected from the group consisting of milk, yogurt, cheese, cream, spread, butter, frozen dessert, and baby formula.

A dairy product comprising therapeutic levels of LCn-3FA, such as DHA, EPA and DPA, is also provided.

In an aspect of the invention, a method of obtaining a dairy product comprising elevated levels of LCn-3FA is provided which comprises feeding to a dairy cow a supplement having at least about 1 g DHA/100 g FA, preferably 1.2 g DHA/100 g FA.

A feed supplement for dairy cows comprising a source of LCn-3FA and a protectant is also provided. In one embodiment, the feed supplement comprises a source of LCn-3FA comprising at least about 1 g. DHA/100 g FA, preferably at least 1.2 g DHA. 100 g FA. In another embodiment, the feed supplement further includes a protectant selected from the group consisting of chitin, chitosan, zeolite, lignin, calcified red seaweed, peat moss, metal salts, an ionophore and combinations thereof.

In another aspect of the invention, a food product comprising elevated LCn-3FA is provided. The food product is preferably selected from the group consisting of soup, sauce, gravy, prepared vegetables, and frozen meals.

BRIEF DESCRIPTION OF THE DRAWINGS

These and other features of the invention will become more apparent from the following description in which reference is made to the appended drawings wherein.

DETAILED DESCRIPTION

The present invention provides a novel dairy product comprising naturally secreted mammalian milk comprising elevated levels of at least one long-chain omega-3 fatty acid, such as at least about 0.3% long chain omega-3 fatty acids/g of total milk fatty acids. In a preferred embodiment, the product comprises at least about 0.3% DHA/g of total milk fatty acids (FA), preferably about 0.35% DHA/g of total milk fatty acids (FA) and more preferably about 0.4% DHA/g of total milk fatty acids (FA), and may additionally comprise at least about 0.1% EPA or DPA/g of total milk FA.

The term "dairy product" as used herein is meant to encompass milk naturally secreted from a mammal, or a product made from such milk, including for example, cheese, yogurt, butter, cream cheese, cottage cheese, sour cream and the like.

The term "long chain omega-3 fatty acid" or "LCn-3FA" is used herein to refer to omega-3 fatty acids comprising at least about 18 carbon atoms, and more preferably at least about 20 carbon atoms, including for example, LCn-3FA such as DHA, EPA, and/or DPA.

The novel dairy product of the present invention may be prepared from milk naturally secreted by ruminant mammals such as cows. The presence of LC n-3 FAs in milk is affected by several factors including, the level of LC n-3 FAs in the diet, total unsaturated FA in the diet, how the FA supply impacts the pathways of lipid biohydrogenation and the presence of other components in the diet that affect rumen biohydrogenation of LCn-3 FA. In this regard, a feed supplement is provided comprising a source of LCn-3FA and a protectant for administration to milk-producing mammals. The supplement, thus, provides an increased level of LCn-3FA in the diet, and the protectant functions to protect LCn-3FAs from rumen biohydrogenation, e.g. prevent or at least reduce rumen biohydrogenation of LCn-3FA, to result in elevated levels of at least one long-chain omega-3 fatty acid, such as at least about 0.3% long chain omega-3 fatty acids/g of total milk fatty acids in the milk secreted by a mammal fed the supplement.

The feed supplement comprises a source of LCn-3FA, preferably comprising at least about 1 g DHA per 100 g FA, and more preferably comprising at least about 1.2 g DHA/100 g FA. Examples of suitable LCn-3FA sources include, but are not limited to, fishmeal, fish oil, krill and algae.

Figure 3:
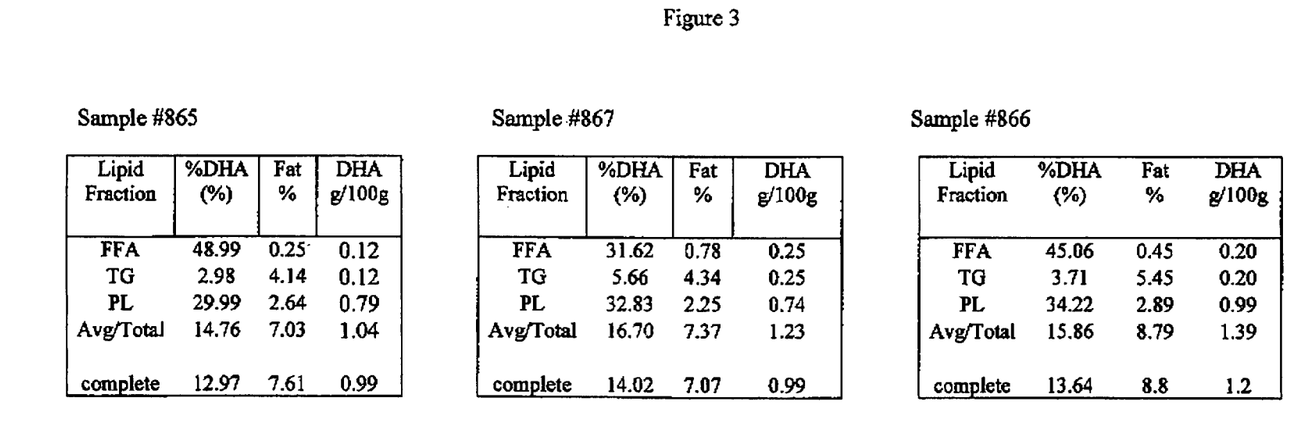
FIG. 3 illustrates the lipid fraction analysis of fishmeal samples.

A preferred source of LC n-3 FAs for use in a LC n-3 FA feed supplement of the invention is fishmeal, preferably comprising at least about 7% FA. In fishmeal, the LC n-3 FAs are present in a variety of forms: free fatty acids (FFA), triglycerides (TG) and phospholipids (PL). Lipid fraction analysis of fishmeals revealed that the form of LC n-3 FAs may vary significantly in different sources. An analysis of these samples is shown in FIG. 3. Preferably, the majority of the DHA in the fishmeal is associated with the phospholipid &/or triglyceride fractions as these FA forms offer greater protection against rumen biohydrogenation than free fatty acids (FFA).

The present feed supplement also comprises a protectant. As used herein, the term "protectant" refers to any feed ingredient that functions to protect LC n-3 FAs from lipid biohydrogenation in the rumen, thereby allowing passage of LCn-3FA to the small intestine for absorption into the blood and subsequent inclusion in other tissues (e.g. mammary gland for incorporation into milk). Protectants may also function to attenuate the possible negative effects associated with feeding unsaturated FAs including LC n-3 FAs (especially at higher levels) to dairy cows (e.g. milk fat depression &/or changes in rumen fermentation). Examples of suitable protectants include, but are not limited to, chitin, chitosan, zeolite, lignin, calcified red seaweed, peat moss e.g. sedge peat moss, salts e.g. metal salts, an ionophore and combinations thereof.

In one embodiment, the protectant is a metal salt, such as a calcium or magnesium salt, that may be used in combination with a LCn-3FA source such as fish oil. In this case, the feed supplement may comprise in the range of about 10-30% metal salt, with the balance of the supplement being fish oil alone, or fish oil combined with additional components such as other LCn-3FA sources, or additives as will be described. Generally, about 40-100 grams/day of this supplement will be given to an animal; however, the amount of supplement will depend on other LCn-3FA and protectant ingredients in the diet, as will be appreciated by one of skill in the art.

In another embodiment, the protectant is an ionophore. The present invention provides, for the first time, the use of an ionophore in a feed to enhance LCn-3FA levels in milk. Suitable ionophores for use in the feed product include monensin, and where approved other ionophores such as lasocid, salinomycin and the like. A preferred ionophore for use in the present invention is monensin. Monensin is a cyclic polyether antibiotic derived from *Streptomycin cinnamonensis*. The feed typically comprises from about 8 to 24 mg monensin per kg of complete diet.

Figure 2:
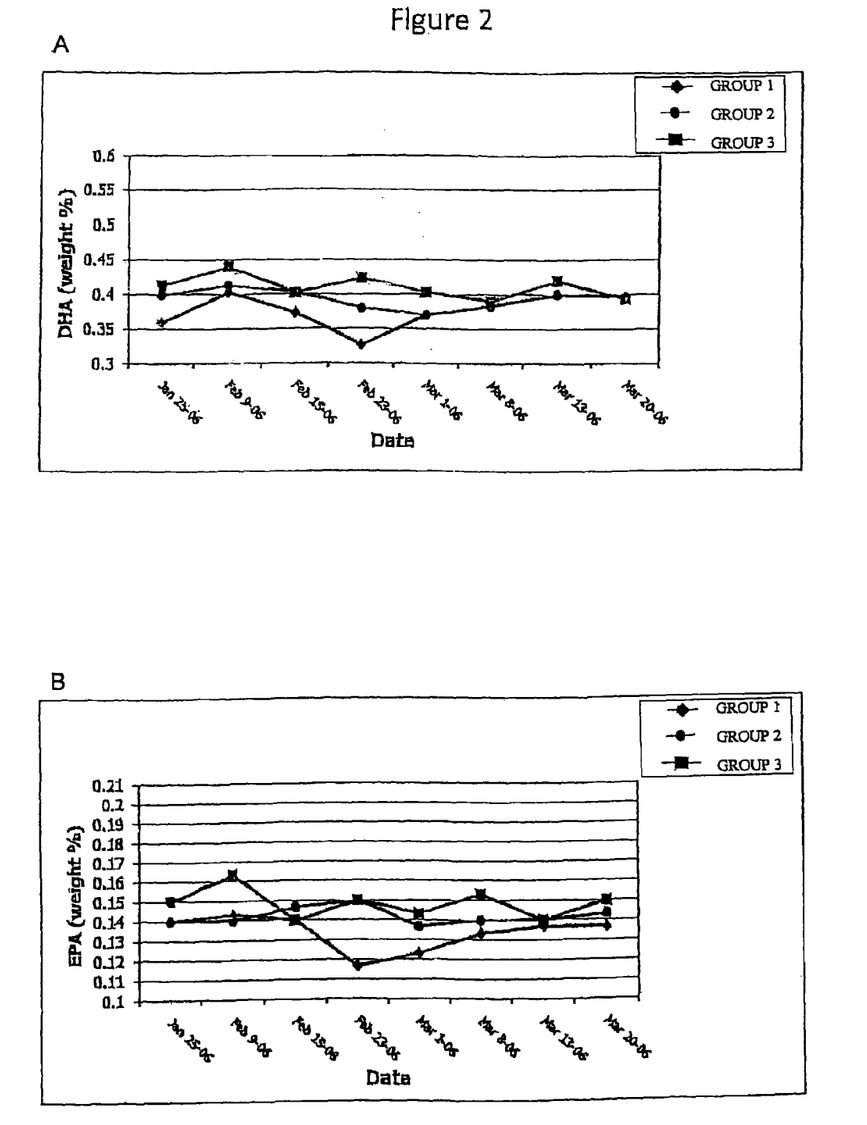
FIG. 2 illustrates graphically the effect of various protectants on LCn-3FA levels in milk.

In a further embodiment of the invention, the protectant is chitin or chitosan. The chitin or chitosan is typically used in the feed in an amount ranging from about 0.25% to 2.0% on a dry weight basis. The results of an exemplary study are shown in FIG. 2. These results demonstrate that chitosan can act as an effective protectant and that its use as a protectant leads to significantly elevated levels of DHA, EPA and DPA in milk secreted by cows to which LCn-3FA feed product containing chitosan are fed.

In yet another embodiment, lignin is used as a protectant to achieve elevated levels of LC n-3 FAs in milk. As used herein, the term "lignin" refers to natural lignin from plant sources and lignin recovered from alkali pulping black liquors such as kraft lignin, soda lignin and the like. The term also encompasses modified lignins. Various polymer sizes of lignin, as well as various molecular forms of lignin can be used. The lignin is typically used in the feed in an amount ranging from about 0.25% to 2.0%, preferably about 0.5 to 1% on a dry weight basis. The results of a field trial where lignin was used as a protectant are also shown in FIG. 2. The results demonstrate that lignins from various sources are effective protectant agents that allow dietary LC n-3 FAs to be transferred to milk.

Porous materials that have the ability to adsorb oils, such as peat moss, calcified red seaweed and zeolite are also useful protectants. For clarity, peat moss, e.g. sedge peat moss, is partial decomposed plant material, derived at least in part from the genus Carex, and is generally used in a dried, ground form. Zeolite is a microporous aluminosilicate mineral commonly used as a commercial adsorbent. Calcified red seaweed is a calcareous marine algae, generally having a honeycomb structure composed of lithothamium calcarem.

In yet another aspect, fishmeal itself may act as a protectant for the LCn-3FA it contains. This enables one to significantly reduce the level of fish meal required in the supplement or reduce the level of other protectants to be added to the supplement. LCn-3FA in fish meal are present in a form that is less susceptible to biohydrogenation, e.g. as phospholipids and/or triglycerides. Accordingly, depending on the quality of fishmeal used, and more specifically the form(s) of FAs present in the fishmeal, the amount of fishmeal in the supplement may be reduced by up to about 10-30%. Thus, if the LCn-3FA in a fish meal is associated with the phospholipid &/or triglyceride fractions, then the amount of fishmeal used may be reduced by an amount at the upper end of this range (e.g. about 20-30%), while LCn-3FA in free fatty acid form may be reduced by an amount at the lower end of this range (e.g. about 10-15%).

The protectants for use in the invention may be used singly or in combination. Combinations of protectants may act additively or synergistically. The cumulative amount of protectant, used either singly or in combination, incorporated in a portion of the feed supplement to be fed to an animal will vary from about 50-200 grams/day. The amount used will depend, at least in part, on the type and amount of LCn-3FA ingredients used in the supplement (e.g. fish oil versus fish meal, etc.). In this regard, a lesser amount of protectant may be used in a supplement comprising fish meal as described, while a greater amount of protectant may be used with other sources of LCn-3FA which do not already comprise a protectant effect.

The invention also provides a method of producing milk having elevated levels of LC n-3 FAs, particularly DHA, EPA and DPA. The method comprises feeding a ruminant milk-producing mammal, such as a dairy cow, a dietary source of LC n-3 FAs. The LC n-3 FAs may be derived from various sources. In a preferred embodiment, the LC n-3 FA source is fishmeal &/or fish oil. DHA is used as a reference point to predict total LC n-3 FA levels. A feed supplement containing LCn-3FA sources preferably comprises at least about 0.5 grams DHA per 100 grams FA, and more preferably, at least about 1.0 gram DHA per 100 grams FA, and most preferably at least about 1.3 grams DHA per 100 grams FA. Animals are fed between about 0.6-1.4 kilograms of an LCn-3FA feed supplement per day, preferably at least about 1 kg of feed supplement per day and most preferably at least about 1.2 kg of feed supplement per day. The LC n-3 FA source(s) is combined with a protectant such as a chitin, chitosan, zeolite, lignin, calcified red seaweed, sedge peat moss, metal salts, an ionophore or mixtures thereof. Animals are fed a nutritionally balanced ration which includes the LCn-3FA feed supplement comprising; i) about 2 to 10% LC n-3 FAs of the feed supplement, preferably 2-8%, more preferably 2-5%; and ii) a protectant or combination of protectants selected from the group consisting of chitin, chitosan, zeolite, lignin, calcified red seaweed, sedge peat moss, metal salts, and/or an ionophore as described.

In a preferred embodiment, the LC n-3 FA source in the feed supplement is fishmeal &/or fish oil. DHA is used as a reference point to predict total LC n-3 FA levels. The LCn-3FA source preferably comprises at least about 1.0 gram DHA per 100 grams FA, and more preferably, at least about 1.2 grams DHA per 100 grams FA. Animals are fed between about 0.8 and 1.2 kilograms of an LCn-3FA source per day comprising between 1-1.2 grams DHA per 100 grams FA. The LC n-3 FA source is combined with a protectant such as a chitin, chitosan, zeolite, lignin, calcified red seaweed, peat moss, metal salts, an ionophore or mixtures thereof in amounts as described.

The LC n-3 FA feed supplement of the invention may be fed either as a top dressing or fed with other feed ingredients as part of a total mixed ration, e.g. admixed with a combination of concentrates (e.g. grains, proteins, minerals, vitamins and some byproduct feeds) and roughages (e.g. fibrous feeds like hay, hay crop silage, corn silage, and the like). An amount of the feed supplement of about 1 to 5 kg, preferably about 1 to 3.5 kg, more preferably about 1.2 kg, per day is suitable to increase LCn-3FA in milk. Additional components such as grains, proteins, vitamins, minerals, buffers and combinations thereof may be combined with the feed supplement in varying amounts depending on the diet required by the animals to which the supplement is being fed and the nutrient content of the additional components. Further, one or more of the components may be absent and other components may be present in the feed supplement. As one of skill in the art will appreciate, amounts of any additional components added to the feed supplement may be adjusted for other ruminants such as goats or sheep, and will be based the nutritional requirement of the animal.

During the transition period from a conventional feeding program to an LC n-3 FA feeding program dairy cows typically take 6 to 12 weeks to achieve levels of DHA in excess of 0.3%/g total milk fat. There may be an associated drop in milk fat content followed by a recovery of the milk fat content to levels close to pre-transition. The extent of the milk fat depression (0-25%) and the nature of the milk fat recovery are unpredictable and vary from herd to herd. Particularly good results in milk fat recovery have been achieved by 10 to 16 weeks after initiation of the LC n-3 FA feeding program.

The invention also encompasses animal products such as milk, milk products (milk solids, milk fat) and processed milk products e.g. cheese and butter, as well as meat, produced from ruminant mammals subjected to the present feed product. Such animal products exhibit enhanced levels of LCn-3FAs including DHA, EPA and DPA. The present invention provides, for the first time, milk containing elevated levels of DHA. The milk of the invention comprises at least 0.3% DHA, preferably at least 0.35% DHA, more preferably at least 0.40% DHA as a percent of total milk FA. A preferred milk also includes at least about 0.1% EPA, 0.1% DPA or both.

Although DHA and other LCn-3FAs are notoriously subject to oxidative degradation, the levels are very stable when secreted in milk. Milk containing elevated levels of DHA according to the invention, withstands ultra high temperature pasteurization and also has a subsequent shelf life in excess of 21 days (see Example 4).

The present invention demonstrates that LCn-3FA levels achieved in milk products by the methods of the invention remain stable for extended periods of time (e.g. levels of LCn-3FA in cheese were not decreased at 3 years, see Example 5). The levels remain stable even when the milk product is further processed such as by high temperature, for example, pasteurization or natural cooking. The milk product can be incorporated into processed foods such as cream, butter, ice cream, cheese, yogurt, soups, sauces, spreads, etc. Prepared foods such as packaged potatoes or pasta and sauce products are also encompassed. This includes dried products. LCn-3FA-enhanced milk products of the invention are particularly useful for inclusion in infant nutritional formulations.

In addition to enhancing the levels of LCn-3FAs in animal-derived products, the feed supplement of the invention provides health benefits to livestock as compared to conventional feeds.

While the methods and compositions of the invention have been described with particular reference to dairy cattle and the production of dairy products, it is clearly apparent that the methods and compositions can also be applied to other ruminants such as beef cattle, sheep and goats.

Dairy farmers are partially compensated based on the percent of fat in milk. A disadvantage of previous feeds containing LC n-3 FAs is that they result in a decrease in the percent of total fat in milk (up to 25% reduction), with no recovery. The compositions and methods of the present invention demonstrate that after an initial milk fat depression in most cases, the original milk fat level can be recovered in time, often within 10 to 16 weeks, to an acceptable level, e.g. a level of at least about 3.5%, and more preferably, a level of at least about 4%. The present invention provides, thus, a feed supplement and a method of feeding dairy cows whereby LC n-3 FAs are fed to the animal and transferred to the milk without decreasing the total amount of fat in the resultant milk.

The present invention will be further illustrated in the following specific examples which are not to be construed as limiting.

EXAMPLES

Example 1

Exemplary LC n-3 FA Feed Supplement

Figure 1:
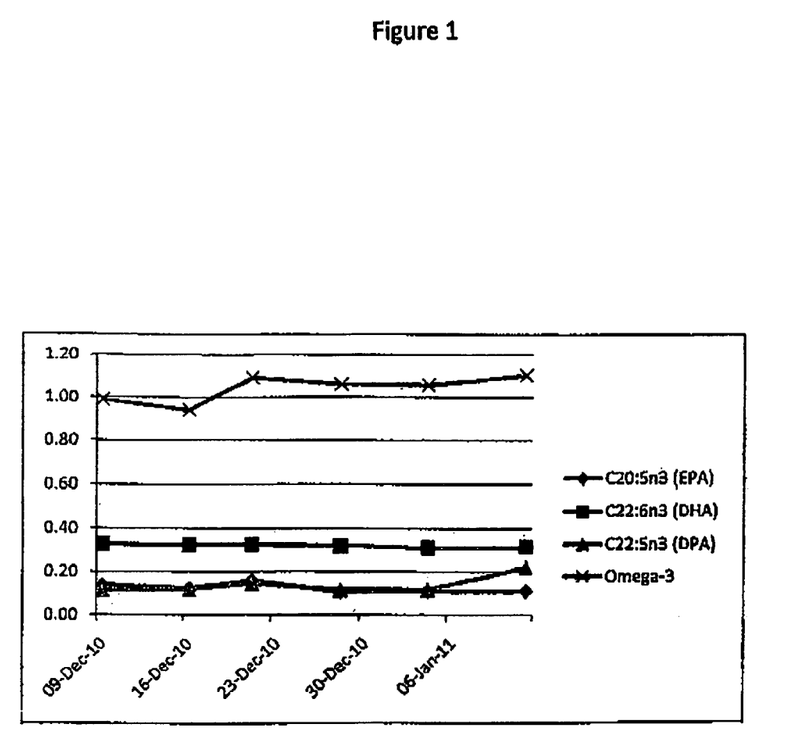
FIG. 1 graphically illustrates EPA, DHA, DPA & total Omega-3 fatty acid levels in milk of cows fed an LC n-3 FA enhanced diet using a protectant combination of zeolite, calcified red seaweed and peat moss.

LC n-3 FA sources; fishmeal (0.9-1 kg/head/day) and fish oil (40 g/head/day) were combined with protectant sources; zeolite (50 g), calcified red seaweed (25 g) and sedge peat moss (50 g) along with other acceptable feed ingredients (concentrates and roughages) to provide a LC n-3 FA feed supplement that enhances the levels of LC n-3 FAs in milk derived from dairy cows fed the supplement. FIG. 1 illustrates the LC n-3 FAs results (specifically DHA, EPA, DPA & total Omega-3 FA) achieved over a 6 week period. Herd milk fat percentage remained normal at greater than 4.0%.

Dairy cows received a daily dose of about 1.2 kg of the LC n-3 FA supplement. Total dose may be altered for other animals.

Example 2

Use of Chitosan as a Protectant

LC n-3 FA sources; fishmeal (1.0 kg/head/day) was combined with protectant; chitosan (25-35 grams/head/day) along with other feed ingredients (concentrates & roughages)

to provide a LC n-3 FA feed supplement that enhances the levels of LC n-3 FAs in milk derived from dairy cows fed the supplement. The milk DHA level (expressed as DHA as % of total milk fatty acids) varied from 0.40 to 0.44% (see FIG. 2). These results demonstrate that chitosan is a very effective protectant that enhances the transfer of dietary LC n-3 FAs to milk.

Example 3

Acceptability of DHA/EPA/DPA Omega-3 Milk

A set of four tests each on of homogenized, 2% and 1% DHA/EPA/DPA Omega-3 milk obtained from cows fed a supplement as described in Example 1 were conducted to determine the degree of organoleptic acceptability of the four milk samples, from the perspective of appearance, flavour, and overall acceptability (e.g. a measure of the level to which the product meets human organoleptic expectations when compared to similar products in the marketplace) versus a control in each case. The results were reported numerically on a nine-point scale, with nine representing 'like extremely' and one representing 'dislike extremely'. Twelve panelists participated in the study. The average results of the tests, along with standard deviations, are shown in the following Table 1.

TABLE 1

|  | Appearance | | Flavour | | Overall | |
| --- | --- | --- | --- | --- | --- | --- |
|  | Control | DHA Milk | Control | DHA Milk | Control | DHA Milk |
| Homo | 7.2 | 7.6 | 6.8 | 7.5 | 6.9 | 7.4 |
| $\sigma$ | 2.6 | 1.5 | 3.4 | 2.6 | 2.7 | 1.8 |
| 2% Milk | 7.2 | 7.5 | 7 | 7.5 | 7.2 | 7.5 |
| $\sigma$ | 2.1 | 0.6 | 2.2 | 1.8 | 2.3 | 1.8 |
| 1% Milk | 7.3 | 7.8 | 7.1 | 7.7 | 7.2 | 7.8 |
| $\sigma$ | 1.9 | 1.2 | 2.6 | 1.5 | 2 | 1.8 |

The results of organoleptic acceptability tests shown above indicated that there was no significant difference between the control and test samples for appearance, flavour and overall acceptability at the 95% confidence level.

Example 4

Analysis of Pasteurized DHA/EPA/DPA Omega-3 Enriched Milk

Analyses of the DHA/EPA/DPA Omega-3 raw milk (obtained from cows fed a supplement as described in Example 1 from 3 different farms in Ontario) was conducted using techniques well-established in the art. The results are set out below in Table 2 as follows:

TABLE 2

| % | Sample 1 | Sample 2 | Sample 3 |
| --- | --- | --- | --- |
| Total Fat | 4.00 | 4.04 | 4.10 |
| Total Protein | 3.48 | 3.44 | 3.47 |
| Total Lactose | 4.80 | 4.85 | 4.85 |
| DHA | 0.32 | 0.35 | 0.32 |
| EPA | 0.15 | 0.15 | 0.16 |
| DPA | 0.17 | 0.18 | 0.19 |
| Total Omega-3 | 1.16 | 1.37 | 1.22 |

A blend of the 3 samples, i.e. an equal amount of each sample was used to form a blend, was used to produce pasteurized fluid milk products (3.25%, 2% and 1% fat DHA/Omega-3 milk). Samples of the fluid milk products were tested for levels of long-chain Omega-3 fatty acids during the shelf-life of each product. The results are set out in Table 3.

TABLE 3

|  | % DHA | % EPA | % DPA | % Omega-3 |
| --- | --- | --- | --- | --- |
| Day 1 | | | | |
| 1% | 0.32 | 0.14 | 0.17 | 1.15 |
| 2% | 0.33 | 0.16 | 0.18 | 1.20 |
| 3.25% | 0.32 | 0.15 | 0.18 | 1.18 |
| Day 7 | | | | |
| 1% | 0.33 | 0.14 | 0.17 | 1.20 |
| 2% | 0.32 | 0.15 | 0.17 | 1.19 |
| 3.25% | 0.32 | 0.16 | 0.18 | 1.18 |
| Day 14 | | | | |
| 1% | 0.32 | 0.13 | 0.16 | 1.18 |
| 2% | 0.32 | 0.15 | 0.18 | 1.20 |
| 3.25% | 0.34 | 0.14 | 0.17 | 1.19 |
| Day 21 | | | | |
| 1% | 0.32 | 0.15 | 0.18 | 1.15 |
| 2% | 0.33 | 0.14 | 0.18 | 1.17 |
| 3.25% | 0.32 | 0.15 | 0.17 | 1.20 |

The above results demonstrate the stability of the Omega-3 fatty acids in DHA/Omega-3 fluid milk during pasteurization, processing and throughout the shelf life of the product.

Example 5

Analysis of Cheese from LCn-3FA Enriched Milk

About 200 kg of DHA/EPA/DPA/Omega-3 enriched raw milk were collected from each of two separate milk farms at which the herds had been fed exclusively with DHA/EPA/DPA/Omega-3 supplement as described in Example 1 for six months. The raw milk collected from each farm was delivered to the University of Guelph pilot plant for manufacturing into cheddar cheese. The chemical analysis of the raw milk was as follows:

TABLE 4

| % | Farm A | Farm B |
| --- | --- | --- |
| Total Fat | 3.84 | 3.52 |
| Total Protein | 3.28 | 3.27 |
| Total Lactose | 4.74 | 4.64 |
| DHA | 0.34 | 0.31 |
| EPA | 0.15 | 0.11 |
| DPA | 0.15 | 0.13 |
| Total Omega-3 | 1.25 | 1.16 |

The raw milk was standardized to 3.1% fat by adding skim milk at 0.21% fat and was then pasteurized. About 170 kg of standardized milk from each farm was used to make a batch of cheddar cheese. After pressing the cheese for 24 hours the two batches were weighed at 17.0 kg and 16.70 kg respectively, and each was cut into pieces of about 1 kg each. The cheese was multivac packaged in plastic bags and stored for aging in a refrigerator at 4° C. The cheese was tested periodically for DHA, EPA and total omega-3, with the following results.

TABLE 5

| | Farm A | | | | Farm B | | | |
| --- | --- | --- | --- | --- | --- | --- | --- | --- |
| | DHA | EPA | DPA | Omega-3 | DHA | EPA | DPA | Omega-3 |
| Day 1 | 0.33% | 0.14% | 0.15% | 1.24% | 0.31% | 0.11% | 0.12% | 1.16% |
| 3 Months | 0.34% | 0.15% | 0.15% | 1.25% | 0.30% | 0.12% | 0.13% | 1.15% |
| 12 Months | 0.33% | 0.15% | 0.16% | 1.13% | 0.31% | 0.11% | 0.13% | 1.14% |
| 24 Months | 0.33% | 0.14% | 0.14% | 1.22% | 0.30% | 0.10% | 0.12% | 1.15% |
| 36 Months | 0.34% | 0.13% | 0.16% | 1.16% | 0.30% | 0.11% | 0.14% | 1.13% |

As can be seen from the above cheese analysis, DHA, EPA, DPA and total Omega-3 are completely stable and unchanged throughout the cheddar cheese aging process.

The present invention has been described with regard to one or more embodiments. However, it will be apparent to persons skilled in the art that a number of variations and modifications can be made without departing from the scope of the invention as defined in the claims.

What is claimed is:

1. A feed supplement for dairy cows comprising fishmeal that comprises at least about 2% to about 10% long chain omega-3 fatty acids wt/wt and at least about 0.5 g DHA/100 g fatty acids, admixed with chitin, chitosan, or combinations thereof, wherein the supplement comprises about 50-200 g of chitin, chitosan or combinations thereof for 0.6-1.4 kilograms of fishmeal.

2. The feed supplement of claim 1, comprising at least about 2% to about 5% long chain omega-3 fatty acids.

3. The feed supplement according to claim 1 wherein the fishmeal comprises at least about 1 g DHA/100 g FA.

4. A method of obtaining naturally secreted mammalian milk comprising at least about 0.3% DHA/g of total milk fatty acids, said method comprising:

i) feeding to a ruminant mammal 0.6-1.4 kilograms per day of a feed supplement for at least 6 weeks, wherein said feed supplement comprises a source of long chain omega-3 fatty acids that comprises at least about 2% to about 10% long chain omega-3 fatty acids wt/wt and at least about 0.5 g DHA/100 g fatty acids, admixed with 50-200 g of chitin, chitosan or a combination thereof; and ii) collecting milk secreted by the mammal comprising at least about 0.3% DHA/g of total milk fatty acids.

* * * * *